United States Patent
Ju et al.

(10) Patent No.: US 10,294,550 B2
(45) Date of Patent: May 21, 2019

(54) HEAT RESISTANT SPHEROIDAL GRAPHITE CAST IRON, METHOD OF MANUFACTURING THE SAME AND ENGINE EXHAUST SYSTEM PART INCLUDING THE SAME

(71) Applicant: Doosan Infracore Co., Ltd., Incheon (KR)

(72) Inventors: Young-Kyu Ju, Seoul (KR); Ki-Hwan Jung, Gyeonggi-do (KR); Jong-Kwon Chung, Gyeonggi-do (KR); Sik Yang, Gyeonggi-do (KR); Jae-Hyoung Hwang, Gyeonggi-do (KR); Dong-Seob Shim, Gyeonggi-do (KR); Sang-Beom Kim, Seoul (KR)

(73) Assignee: DOOSAN INFRACORE CO., LTD, Incheon (KR)

( * ) Notice: Subject to any disclaimer, the term of this patent is extended or adjusted under 35 U.S.C. 154(b) by 217 days.

(21) Appl. No.: 15/125,477

(22) PCT Filed: Feb. 6, 2015

(86) PCT No.: PCT/KR2015/001253
§ 371 (c)(1),
(2) Date: Sep. 12, 2016

(87) PCT Pub. No.: WO2015/137627
PCT Pub. Date: Sep. 17, 2015

(65) Prior Publication Data
US 2017/0073798 A1    Mar. 16, 2017

(30) Foreign Application Priority Data
Mar. 12, 2014   (KR) .................. 10-2014-0028909

(51) Int. Cl.
C22C 37/10 (2006.01)
C22C 37/06 (2006.01)
(Continued)

(52) U.S. Cl.
CPC .............. C22C 37/10 (2013.01); B22D 17/00 (2013.01); B22D 25/02 (2013.01); C21C 1/105 (2013.01);
(Continued)

(58) Field of Classification Search
CPC ........ B22D 17/00; B22D 25/02; C21C 1/105; C21D 2211/004; C21D 2211/005;
(Continued)

(56) References Cited

U.S. PATENT DOCUMENTS

| | | | |
|---|---|---|---|
| 2006/0191508 A1* | 8/2006 | Otsuka | B22D 30/00 123/193.6 |
| 2011/0132314 A1* | 6/2011 | Muller | B22D 19/0009 123/193.5 |

(Continued)

FOREIGN PATENT DOCUMENTS

| | | |
|---|---|---|
| EP | 2377960 | 10/2011 |
| JP | H09-170041 A | 6/1997 |

(Continued)

OTHER PUBLICATIONS

International Search Report (with English translation) issued in international application No. PCT/KR2015/001253, dated May 22, 2015, 5 pages.

(Continued)

*Primary Examiner* — Ngoc-Yen Nguyen
(74) *Attorney, Agent, or Firm* — K&L Gates LLP

(57) ABSTRACT

Heat resistant spheroidal graphite cast iron having an improved high temperature tensile strength includes carbon (C) in a range of 3.2-3.4 wt %, silicon (Si) in a range of (Continued)

4.3-4.8 wt %, manganese (Mn) in a range of 0.2-0.3 wt %, molybdenum (Mo) in a range of 0.8-1.0 wt %, vanadium (V) in a range of 0.4-0.6 wt %, chrome (Cr) in a range of 0.2-0.4 wt %, niobium (Nb) in a range of 0.2-0.4 wt %, inevitable impurities, and a remainder of iron (Fe) based on a total weight of the heat resistant spheroidal graphite cast iron. The heat resistant spheroidal graphite cast iron further includes barium (Ba) in a range of 0.0045-0.0075 wt %. A content ratio of chrome (Cr) and barium (Ba) (Cr/Ba) is in a range from about 26 to about 89.

9 Claims, 5 Drawing Sheets

(51) Int. Cl.

| | | |
|---|---|---|
| C22C 33/08 | (2006.01) | |
| G01N 25/00 | (2006.01) | |
| B22D 25/02 | (2006.01) | |
| F01N 13/14 | (2010.01) | |
| G01N 33/20 | (2019.01) | |
| H01J 49/26 | (2006.01) | |
| B22D 17/00 | (2006.01) | |
| C22C 37/04 | (2006.01) | |
| G01N 33/205 | (2019.01) | |
| C22C 33/04 | (2006.01) | |
| C21C 1/10 | (2006.01) | |
| C21D 5/00 | (2006.01) | |

(52) U.S. Cl.
CPC .............. *C22C 33/04* (2013.01); *C22C 33/08* (2013.01); *C22C 37/04* (2013.01); *C22C 37/06* (2013.01); *F01N 13/14* (2013.01); *G01N 25/00* (2013.01); *G01N 33/205* (2019.01); *H01J 49/26* (2013.01); *C21D 5/00* (2013.01); *C21D 2211/004* (2013.01); *C21D 2211/005* (2013.01); *C21D 2211/009* (2013.01); *F01N 2510/02* (2013.01)

(58) Field of Classification Search
CPC ..... C21D 2211/009; C21D 5/00; C22C 33/04; C22C 33/08; C22C 37/04; C22C 37/06; C22C 37/10; F01N 2510/02; G01N 25/00; G01N 33/205; H01J 49/26
See application file for complete search history.

(56) References Cited

U.S. PATENT DOCUMENTS

| | | | |
|---|---|---|---|
| 2011/0211986 A1 | 9/2011 | Arai | |
| 2015/0336353 A1* | 11/2015 | Oda | ........................ B21B 27/00 492/3 |

FOREIGN PATENT DOCUMENTS

| | | |
|---|---|---|
| JP | H11-229072 A | 8/1999 |
| JP | 2007-029968 A | 2/2007 |
| JP | 2011-012313 | 1/2011 |
| KR | 10-2007-002880 | 3/2007 |
| KR | 10-2009-0018462 A | 2/2009 |
| KR | 10-2011-0069170 A | 6/2011 |
| WO | 2009025456 | 2/2009 |

OTHER PUBLICATIONS

Written Opinion issued in international application No. PCT/KR2015/001253, dated May 22, 2015, 8 pages.
Office Action issued in related Chinese Patent Application No. 201580013206.0 dated May 10, 2017. 8 pages.
Extended European Search Report issued in corresponding European Patent Application No. 15760658.3 dated Jul. 17, 2017. 11 pages.
C. Labrecque et al., "Ductile Iron: Fifty Years of Continuous Development," Canadian Metallurgical Quarterly, No. 37, No. 5, Jan. 1, 1998, pp. 343-378.

* cited by examiner

HEAT RESISTANT SPHEROIDAL GRAPHITE CAST IRON, METHOD OF MANUFACTURING THE SAME AND ENGINE EXHAUST SYSTEM PART INCLUDING THE SAME

CROSS REFERENCE TO RELATED APPLICATIONS

The present application is a National Stage of International Application No. PCT/KR2015/001253, filed on Feb. 6, 2015, which claims priority to Korean Patent Application No. 10-2014-0028909, filed on Mar. 12, 2014, the entire contents of each of which are being incorporated herein by reference.

BACKGROUND

1. Field

The present inventive concepts relate to heat resistant spheroidal graphite cast iron, a method of manufacturing the same, and an engine exhaust system including the same. More particularly, the present inventive concepts relate to heat resistant spheroidal graphite cast iron having a specific composition ratio and excellent high temperature material properties (for example, eutectoid transformation temperature and high temperature tensile strength), a method of manufacturing the same, and an engine exhaust system including the same.

2. Description of the Related Art

Recently, as demands for improved fuel efficiency are increased and environment-related restrictions are becoming strengthened globally, an engine operates with high power, resulting in an increase of a combustion temperature in an exhaust system component. As such, in order to meet continued demands for corresponding to the increased combustion temperature in a heat resistant part, a heat resistant material having an excellent heat resistant property is being developed necessarily.

Heat resistant spheroidal graphite cast iron including silicon (Si) and molybdenum (Mo) is a representative material used for a vehicle exhaust system component which is required to have excellent high temperature properties. In order to increase eutectoid transformation temperature of the heat resistant spheroidal graphite cast iron and precipitate carbide at high temperature to maintain high strength, silicon (Si) content may be increased and a carbide forming element such as molybdenum (Mo) may be added, respectively.

Especially, in order to maintain desired material properties at the combustion temperature of above 800° C. in the exhaust system, a heat resistant property may be required to have more excellent high temperature material property and lower coefficient of thermal expansion than a widely used Si—Mo based heat resistant spheroidal graphite cast iron.

Studies have been conducted to improve a heat resistant property of a material based on the Si—Mo based heat resistant spheroidal graphite cast iron. Conventionally, in order to improve the heat resistant property, a carbide forming element and an additional alloy element was added, however, during alloy design about a selection of alloy element and an addition rate, quantitative reviews on precipitate prediction was insufficient. Thus, a development level of the conventional Si—Mo based heat resistant spheroidal graphite cast iron was low to the extent that high temperature tensile strength at 700° C. was about 70-80 Mpa and high temperature tensile strength at 800° C. was about 45-58 Mpa. In a conventional art, there was a limit to improve high temperature material properties such as high temperature tensile strength, and it was difficult to apply mass production because of matrix structure instability. Because an increase of high temperature tensile strength can greatly affect a product's stability, various researches are required to be conducted in order to improve high temperature material properties.

SUMMARY

To overcome the problems as discussed above, example embodiments provide heat resistant spheroidal graphite cast iron having an excellent heat resistant property.

Example embodiments provide a method of manufacturing heat resistant spheroidal graphite cast iron having an excellent heat resistant property.

Example embodiments provide an engine component and exhaust system including heat resistant spheroidal graphite cast iron having an excellent heat resistant property.

According to example embodiments, in a method of manufacturing heat resistant spheroidal graphite cast iron, a molten cast iron is formed, the molten cast iron including carbon (C) in a range from about 3.2 weight percent to about 3.4 weight percent, silicon (Si) in a range from about 4.3 weight percent to about 4.8 weight percent, manganese (Mn) in a range from about 0.2 weight percent to about 0.3 weight percent, molybdenum (Mo) in a range from about 0.8 weight percent to about 1.0 weight percent, vanadium (V) in a range from about 0.4 weight percent to about 0.6 weight percent, chrome (Cr) in range from about 0.2 weight percent to about 0.4 weight percent, niobium (Nb) in a range from about 0.2 weight percent to about 0.4 weight percent, inevitable impurities, and a remainder of iron (Fe), based on a total weight. The molten cast iron is tapped into a ladle. The tapped molten cast iron is injected into a mold.

In example embodiments, the method may further include, prior to injecting the tapped molten cast iron into the mold, adding barium (Ba) into the molten cast iron. A content ratio of chrome (Cr) and barium (Ba) (Cr/Ba) may be in a range from about 26 to about 89.

In example embodiments, barium (Ba) may be in a range from about 0.0045 weight percent to about 0.0075 weight percent based on a total weight.

In example embodiments, forming the molten cast iron may include forming an original molten cast iron including carbon (C) in a range from about 3.2 weight percent to about 3.4 weight percent, silicon (Si) in a range from about 4.3 weight percent to about 4.8 weight percent, manganese (Mn) in a range from about 0.2 weight percent to about 0.3 weight percent, inevitable impurities, and a remainder of iron (Fe), based on a total weight, and adding molybdenum (Mo) in a range from about 0.8 weight percent to about 1.0 weight percent, vanadium (V) in a range from about 0.4 weight percent to about 0.6 weight percent, chrome (Cr) in range from about 0.2 weight percent to about 0.4 weight percent and niobium (Nb) in a range from about 0.2 weight percent to about 0.4 weight percent, based on a total weight, into the original molten cast iron.

In example embodiments, tapping the molten cast iron into the ladle may include adding a first inoculant into the molten cast iron. Injecting the tapped molten cast iron into the mold may include adding a second inoculant into the molten cast iron.

In example embodiments, forming the molten cast iron may include forming a preliminary molten cast iron, analyzing the preliminary molten cast iron by a thermal analysis or a mass spectrometer, and adding a deficient ingredient into the preliminary molten cast iron.

According to example embodiments, heat resistant spheroidal graphite cast iron includes carbon (C) in a range from about 3.2 weight percent to about 3.4 weight percent, silicon (Si) in a range from about 4.3 weight percent to about 4.8 weight percent, manganese (Mn) in a range from about 0.2 weight percent to about 0.3 weight percent, molybdenum (Mo) in a range from about 0.8 weight percent to about 1.0 weight percent, vanadium (V) in a range from about 0.4 weight percent to about 0.6 weight percent, chrome (Cr) in range from about 0.2 weight percent to about 0.4 weight percent, niobium (Nb) in a range from about 0.2 weight percent to about 0.4 weight percent, inevitable impurities, and a remainder of iron (Fe), based on a total weight of the heat resistant spheroidal graphite cast iron.

In example embodiments, the heat resistant spheroidal graphite cast iron may have tensile strength of about 670 Mpa or more at a room temperature, and may have high temperature tensile strength of 100 Mpa or more at 700° C. and of 60 Mpa or more at 800° C.

In example embodiments, the heat resistant spheroidal graphite cast iron may have coefficient of thermal expansion of about 13.5 μm/m·° C. or less, and may have eutectoid transformation temperature of from about 920° C. to about 940° C.

In example embodiments, the heat resistant spheroidal graphite cast iron may further include barium (Ba) in a range from about 0.0045 weight percent to about 0.0075 weight percent. A content ratio of chrome (Cr) and barium (B a) (Cr/B a) may be in a range from about 26 to about 89.

In example embodiments, the heat resistant spheroidal graphite cast iron may have high temperature tensile strength of from 59 Mpa to 70 Mpa at 800° C.

In example embodiments, the heat resistant spheroidal graphite cast iron may include a ferrite structure occupying an area of about 50% or more in a total area.

According to example embodiments, an engine exhaust system includes an exhaust manifold having the above-mentioned heat resistant spheroidal graphite cast.

According to example embodiments of the present inventive concepts, heat resistant spheroidal graphite cast iron may include additional elements such as vanadium (V), chrome (Cr) and niobium (Nb) capable of forming carbide. The content of the additional elements may be precisely controlled to improve high temperature material properties such as high temperature tensile strength without reducing ductility. In addition, the heat resistant spheroidal graphite cast iron may further include barium (Ba) in addition to vanadium (V), chrome (Cr) and niobium (Nb). Especially, a content ratio of chrome (Cr) and barium (B a) may controlled such that chrome carbide showing embrittlement at a room temperature may be prevented from being generated and graphite nucleation creation may be facilitated, to thereby provide the heat resistant spheroidal graphite cast iron having a stable material property and structure. Because the heat resistant spheroidal cast iron has an improved high temperature tensile strength, the heat resistant spheroidal graphite cast iron may be effectively implemented to an exhaust manifold in an engine exhaust system which operates under high temperature.

BRIEF DESCRIPTION OF THE DRAWINGS

Example embodiments will be more clearly understood from the following detailed description taken in conjunction with the accompanying drawings which represent non-limiting, example embodiments as described herein.

DESCRIPTION OF EMBODIMENTS

Figure 1:
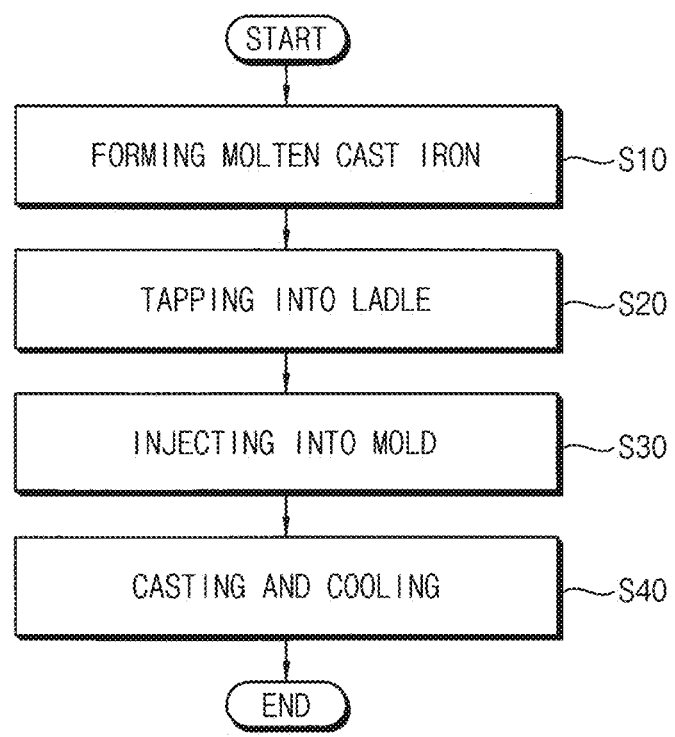
FIG. 1 is a flow chart illustrating a method of manufacturing heat resistant spheroidal graphite cast iron in accordance with example embodiments.

Various example embodiments will be described. The present inventive concept may, however, be embodied in many different forms and should not be construed as limited to the example embodiments set forth herein. Rather, these example embodiments are provided so that this description will be thorough and complete, and will fully convey the scope of the present inventive concept to those skilled in the art.

Since many modifications are possible in example embodiments, a few example embodiments will be described with reference to the accompanying drawings. However, many modifications are possible in example embodiments without materially departing from the novel teachings and advantages of the present invention. Accordingly, all such modifications are intended to be included within the scope of the present inventive concepts.

According to example embodiments of the present inventive concepts, vanadium (V), chrome (Cr) and niobium (Nb) may be added to Si—Mo based heat resistant spheroidal graphite cast iron, and a content ratio of vanadium (V), chrome (Cr) and niobium (Nb) may be controlled to thereby provide heat resistant spheroidal graphite cast iron having an excellent high temperature material property. Further, barium (Ba) may be additionally added to the spheroidal cast iron and a content ratio of barium and chrome may controlled to thereby improve a high temperature material property such as high temperature tensile strength.

Hereinafter, chemical composition of a spheroidal graphite cast iron in accordance with example embodiments and methods of manufacturing the spheroidal graphite cast iron will be described.

First Composition of Heat Resistant Spheroidal Graphite Cast Iron

According to example embodiments, a first composition of heat resistant spheroidal graphite cast iron may include some additional elements in addition to elements of the Si—Mo based heat resistant spheroidal graphite cast iron, thereby achieving an improved heat resistant property.

For example, the Si—Mo based heat resistant spheroidal graphite cast iron may include iron (Fe), carbon (C), silicon (Si), molybdenum (Mo), phosphorous (P) and sulfur (S). In here, an amount of silicon (Si) may be limited so as to prevent graphite shape defects due to high silicon content.

Examples of the additional elements may be vanadium (V), chrome (Cr), niobium (Nb), etc. The amount of vanadium (V), chrome (Cr) and niobium (Nb) may be determined in consideration of improvement effect of the heat resistant property, solid solubility thereof, etc. That is, the amount of vanadium (V), chrome (Cr) and niobium (Nb) may be an important factor in determining the heat resistant property of the heat resistant spheroidal graphite cast iron.

Hereinafter, the amount of each element may be referred to as weight percent (wt %) based on a total weight of the heat resistant spheroidal graphite cast iron.

The heat resistant spheroidal graphite cast iron according to example embodiments may include carbon (C) in a range from about 3.2 weight percent (wt %) to about 3.4 wt %, silicon (Si) in a range from about 4.3 wt % to about 4.8 wt %, manganese (Mn) in a range from about 0.2 wt % to about 0.3 wt %, molybdenum (Mo) in a range from about 0.8 wt % to about 1.0 wt %, vanadium (V) in a range from about 0.4 wt % to about 0.6 wt %, chrome (Cr) in a range from about 0.2 wt % to about 0.4 wt %, niobium (Nb) in a range from about 0.2 wt % to about 0.4 wt %, and a remainder of iron (Fe), based on a total weight of the spheroidal graphite cast iron.

On the other hand, since phosphorous (P) and sulfur (S) are contained in a raw material of the heat resistant spheroidal graphite cast iron, a trace of phosphorous (P) and sulfur (S) may remain naturally in the heat resistant spheroidal graphite cast iron even through these elements (P, S) are not added. Additionally, magnesium (Mg) may be added during Mg treatment (that is, spheroidization process) in manufacturing of the heat resistant spheroidal graphite cast iron.

Hereinafter, each element contained in the heat resistant spheroidal graphite cast iron and an amount of each element will be described in more detail.

1) Silicon (Si) in a Range from about 4.3 wt % to about 4.8 wt %

Silicon (Si) may increase a crystallized amount of graphite by carbon (C) and may be effective in inducing a matrix of ferrite. Additionally, silicon content of the heat resistant spheroidal graphite cast iron may be increased to thereby improve a heat resistant property and oxidation-resistive property. If an amount of silicon (Si) in the heat resistant spheroidal graphite cast iron according to example embodiments is less than about 4.3 wt %, eutectoid transformation temperature may be decreased. If the amount of silicon (Si) exceeds about 4.8 wt %, castability and fluidity may be reduced.

2) Manganese (Mn) in a Range from about 0.2 wt % to about 0.3 wt %

Manganese (Mn) may be one of the basic essentials. This may be because manganese (Mn) reacts with sulfur (S) contained essentially in the raw material of the heat resistant spheroidal graphite cast iron and fixes sulfur (S) as a form of MnS, thereby suppressing adverse effects of sulfur (S). Additionally, the ferrite inducement of the matrix may be strengthened by solid solution strengthening, and creation of carbide may be increased to thereby facilitate a precipitation of pearlite in the matrix. In low oxygen (low 0) and low sulfur (low S) heat resistant spheroidal graphite cast iron, even though manganese (Mn) content is increased, a deterioration of ductility may be small. In the heat resistant spheroidal graphite cast iron in accordance with example embodiments, if the amount of manganese (Mn) exceeds about 0.3 wt %, the precipitation of pearlite in the matrix may be facilitated excessively, and thus, brittleness may be drastically increased and workability may be deteriorated.

3) Molybdenum (Mo) in a Range from about 0.8 wt % to about 1.0 wt %

Molybdenum (Mo) may reinforce tensile strength and yield strength at a high temperature, thereby improving thermal crack resistance, like nickel (Ni). Additionally, molybdenum (Mo) may improve mechanical properties such as heat resistant crackability, like vanadium (V). In the heat resistant spheroidal graphite cast iron in accordance with example embodiments, if the amount of molybdenum (Mo) is less than about 0.8%, an improvement effect of heat resistant property may not be sufficiently achieved. If the amount of molybdenum (Mo) exceeds about 1.0 wt %, elongation percentage may be decreased and hardness may be increased by increased ratios of carbide and pearlite, and thus, machinability may be deteriorated.

4) Chrome (Cr) in a Range from about 0.2 wt % to about 0.4 wt %

Chrome (Cr) may improve thermal crack resistance due to an oxidation-resistive property improvement and a strengthening of the matrix of pearlite. That is, chrome (Cr) may be added to achieve improvement of oxidation-resistive property and high temperature tensile strength, in order for a use in a high temperature. In the heat resistant spheroidal graphite cast iron in accordance with example embodiments, if the amount of chrome (Cr) is less than about 0.2%, an improvement effect of heat resistant property and oxidation-resistive property may not be achieved. If the amount of chrome (Cr) exceeds about 0.4 wt %, hardness may be increased by increased ratios of carbide, and thus, machinability may be deteriorated and fluidity may be reduced.

5) Vanadium (V) in a Range from about 0.4 wt % to about 0.6 wt %

Vanadium (V) may improve strength at a range of from a room temperature to a high temperature of about 850° C. Vanadium (V) may create a fine vanadium carbide (VC) having a high melting point in a ferrite matrix to prevent strain due to stress at a high temperature, to thereby improve high temperature tensile strength. Specifically, vanadium (V) in the range from about 0.4 wt % to about 0.6 wt % may improve the high temperature tensile strength without reducing ductility. If an amount of vanadium (V) exceeds about 0.6 wt %, coarse vanadium carbide may be segregated between process cells to increase hardness and brittleness without improving the high temperature tensile strength.

6) Niobium (Nb) in a Range from about 0.2 wt % to about 0.4 wt %

Niobium (Nb) may refine a grain, and improve mechanical properties such as tensile strength, impact strength, etc. Specifically, niobium (Nb) may have a good affinity to carbon or nitrogen to induce a precipitation of carbide such as niobium carbide in a cast iron, and may suppress a phase transition of ostenite and ferrite ($\gamma/\alpha$).

The heat resistant spheroidal graphite cast iron according to example embodiments may include vanadium (V), chrome (Cr) and niobium (Nb), when compared with a conventional cast iron. Vanadium (V), chrome (Cr) and niobium (Nb) may precipitate carbide or carbonitride, to improve heat resistant property of the spheroidal graphite cast iron.

Second Composition of Heat Resistant Spheroidal Graphite Cast Iron

According to example embodiments, a second composition of heat resistant spheroidal graphite cast iron may include an additional element in addition to elements of the first composition of heat resistant spheroidal graphite cast iron as mentioned above. For example, the additional element may be barium (Ba).

Thus, the second composition of the heat resistant spheroidal graphite cast iron may include carbon (C) in a range from about 3.2 weight percent (wt %) to about 3.4 wt %, silicon (Si) in a range from about 4.3 wt % to about 4.8 wt %, manganese (Mn) in a range from about 0.2 wt % to about 0.3 wt %, molybdenum (Mo) in a range from about 0.8 wt % to about 1.0 wt %, vanadium (V) in a range from about 0.4 wt % to about 0.6 wt %, chrome (Cr) in a range from about 0.2 wt % to about 0.4 wt %, niobium (Nb) in a range from about 0.2 wt % to about 0.4 wt %, barium (Ba) in a range from about 0.0045 wt % to about 0.0075 wt % and a remainder of iron (Fe), based on a total weight of the spheroidal graphite cast iron. In here, a trace amount of barium (Ba) may be used as an ingredient of the cast iron, and a content ratio of chrome (Cr) and barium (Ba) (Cr/Ba) may be in a range from about 26 to about 89. The content of barium may be detected by ICP (inductively coupled plasma) chemical analysis.

When the amounts of chrome (Cr) and barium (Ba) in the cast iron may be controlled in a specific range, inoculation ability may be maximized and they may serve as a nucleation site of spheroidal graphite to suppress a chill phenomenon and assist growth and precipitation of a robust graphite, to thereby achieve excellent high temperature tensile strength and machinability.

Hereinafter, barium (Ba) contained in the heat resistant spheroidal graphite cast iron and an amount of barium will be described in more detail.

1) Barium (Ba) in a Range from about 0.0045 wt % to about 0.0075 wt %

Barium (Ba) may delay and prevent a fading behavior generated in manufacturing of the heat resistant spheroidal graphite cast iron and crystallize a larger number of spheroidal graphite. If an amount of barium (Ba) is less than about 0.0045%, crystallization of oxide may be mainly induced and graphite forming ability may be decreased to thereby facilitate a chill phenomenon. If the amount of barium (Ba) exceeds about 0.0075 wt %, the number of eutectic cells may be reduced, effects on the inoculation may be decreased, and a fading preventing effect may be reduced.

Barium (Ba) may improve thermal crack resistance due to an oxidation-resistive property improvement and a strengthening of the matrix of pearlite. That is, barium (Ba) may be added to achieve improvement of oxidation-resistive property and high temperature tensile strength, in order for a use in a high temperature. In the heat resistant spheroidal graphite cast iron in accordance with example embodiments, if the amount of chrome (Cr) is less than about 0.2%, an improvement effect of heat resistant property and oxidation-resistive property may not be achieved. If the amount of chrome (Cr) exceeds about 0.4 wt %, hardness may be increased by increased ratios of carbide, and thus, machinability may be deteriorated and fluidity may be reduced.

In addition, the content ratio of chrome (Cr) and barium (Ba) (Cr/Ba) may be limited to be in a range from about 26 to about 89. If the content ratio (Cr/Ba) is outside the range 26-89, high temperature tensile strength may be decreased, and machinability and fluidity may be deteriorated due to supersaturated chrome carbide. On the other hand, since phosphorous (P) and sulfur (S) are contained in a raw material of the heat resistant spheroidal graphite cast iron, a trace of phosphorous (P) and sulfur (S) may remain naturally in the heat resistant spheroidal graphite cast iron even through these elements (P, S) are not added. Further, magnesium (Mg) may be added during Mg treatment in manufacturing of the heat resistant spheroidal graphite cast iron.

The heat resistant spheroidal graphite cast iron in accordance with example embodiments may include barium (Ba) in addition to vanadium (V), chrome (Cr) and niobium (Nb). The content ratio of chrome (Cr) and barium (Ba) may be controlled such that chrome carbide showing embrittlement at a room temperature may be prevented from being generated and graphite nucleation creation may be facilitated, to thereby provide heat resistant spheroidal graphite cast iron having a stable material property and structure.

Method of Manufacturing Heat Resistant Spheroidal Graphite Cast Iron

Figure 2:
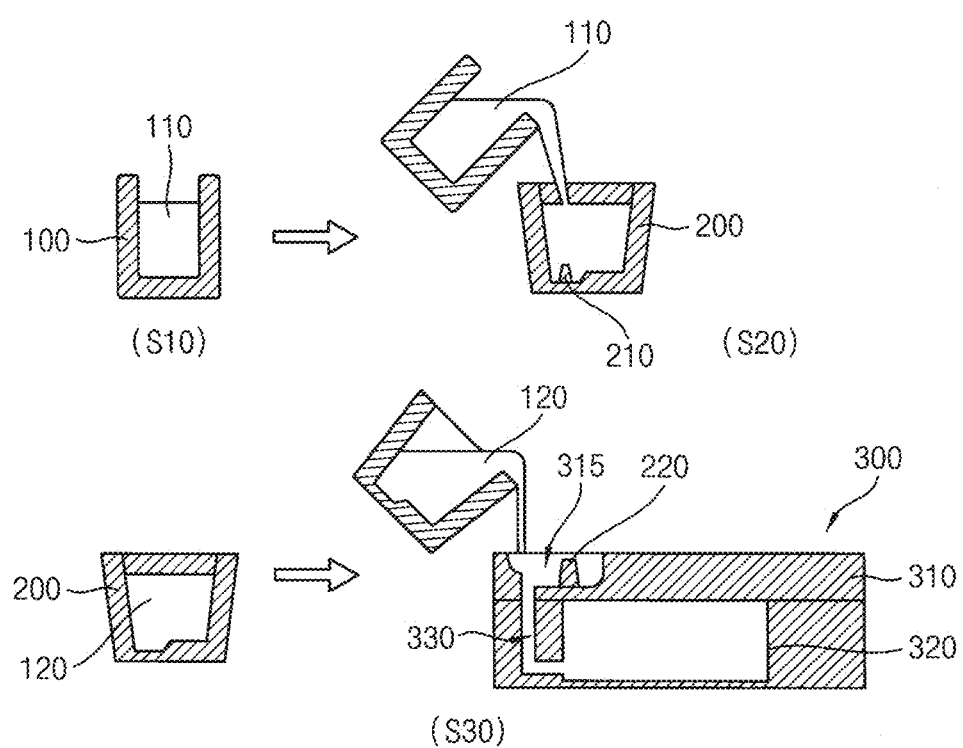
FIG. 2 is a process schematic diagram illustrating the method of manufacturing heat resistant spheroidal graphite cast iron in accordance with example embodiments.

FIG. 1 is a flow chart illustrating a method of manufacturing heat resistant spheroidal graphite cast iron in accordance with example embodiments. FIG. 2 is a process schematic diagram illustrating the method of manufacturing heat resistant spheroidal graphite cast iron in accordance with example embodiments.

Referring to FIGS. 1 and 2, a cast iron raw material may be melted in a melting furnace 100 to form a first molten cast iron 110 (S10).

In example embodiments, the first molten cast iron 110 may include cast iron ingredients such as carbon (C), silicon (Si), manganese (Mn), phosphorous (P) and sulfur (S). The first molten cast iron 110 may include carbon (C) in a range from about 3.2 weight percent (wt %) to about 3.4 wt %, silicon (Si) in a range from about 4.3 wt % to about 4.8 wt % and manganese (Mn) in a range from about 0.2 wt % to about 0.3 wt % based on a total weight of the manufactured heat resistant spheroidal graphite cast iron. Phosphorous (P) and sulfur (S) may be contained naturally in the raw material of the cast iron.

In example embodiments, the first molten cast iron 110 may include additional elements such as vanadium (V), chrome (Cr) and niobium (Nb). In some embodiments, the first molten cast iron 110 may include vanadium (V) in a range from about 0.4 wt % to about 0.6 wt %, chrome (Cr) in a range from about 0.2 wt % to about 0.4 wt % and niobium (Nb) in a range from about 0.2 wt % to about 0.4 wt % based on the total weight of the manufactured heat resistant spheroidal graphite cast iron.

The first molten cast iron 110 may include the cast iron ingredients, the additional elements and a remainder of iron (Fe).

In some embodiments, the cast iron ingredients and the additional elements may be formed as the first molten cast iron 110. In other embodiments, the cast iron ingredients may be formed as an original molten cast iron, and then, the additional elements may be added to the original molten cast iron to form the first molten cast iron 110.

In example embodiments, after a preliminary molten cast iron 110 may be formed, a component analysis may be performed on the preliminary molten cast iron by a thermal analysis or a mass spectrometer and then a deficient ingredient may be added to form the first molten cast iron 110 having the above content ratios.

Then, the first molten cast iron 110 may be tapped into a ladle 200 (S20). During the tapping process, Mg treatment (that is, spheroidization process) may be performed and a first inoculation process may be performed using a first inoculant 210 concurrently with the tapping process.

In example embodiments, the first inoculant 210 may include a Fe—Si-based inoculant. In some embodiments, a trace of barium (B a) may be added in the first inoculation process. For example, an amount of the barium (Ba) may be in a range from about 0.0045 wt % to about 0.0075 wt % based on the total weight of the manufactured heat resistant spheroidal graphite cast iron.

The first inoculation process may be performed on the first molten cast iron 110 within the ladle 200 to obtain a second molten cast iron 120.

In some embodiments, a component analysis may be performed on the second molten cast iron 120 by a thermal analysis or a mass spectrometer and then a deficient ingredient may be added to obtain the above content ratios. Thus, the deficient ingredient which is dissipated during the tapping process may be compensated. For example, the contents of chrome (Cr) and barium (Ba) may be adjusted precisely. A content ratio of chrome (Cr) and barium (Ba) (Cr/Ba) may be in a range from about 26 to about 89.

Then, the second molten cast iron 120 may be injected into a mold 300 (S30). In example embodiments, a second inoculation process may be performed using a second inoculant 220 concurrently with the injecting process into the mold 300.

The mold 300 may include an injection portion 310 and a mold body 320. The injection portion 310 may be integrally formed with the mold body 320.

In some embodiments, the second inoculation process may be performed using mold 310 having a pouring basin 315. The pouring basin 315 may be provided in the injection portion 310. The second molten cast iron 120 may stay temporarily in the pouring basin 315, and the second inoculant 220 may be disposed in the pouring basin 315.

The second inoculant 220 may be formed from a material substantially the same as or similar to the first inoculants 210. For example, the first inoculant 210 may include a Fe—Si-based inoculant.

As the second inoculation process may be performed using the second inoculant 220, the second molten cast iron 120 may be transformed into a cast iron melting solution.

In some embodiments, the mold 300 may include an injection passage 330 through which a liquid flows from the pouring basin 315 into the mold body 320. The cast iron melting solution may be injected into the mold body 320 through the injection passage 330.

Then, the cast iron may be casted within the mold body 320 for a predetermined time, and then, may be cooled by a cooling process to manufacture a final heat resistant spheroidal graphite cast iron (S40). The heat resistant spheroidal graphite cast iron may be effectively implemented to an engine exhaust system component such as an exhaust manifold.

Examples and Comparative Examples

First, in manufacturing of the heat resistant spheroidal graphite cast iron, according to the compositions of Table 1, an original molten metal containing carbon (C), silicon (Si), manganese (Mn), sulfur (S) and phosphorous (P) was prepared. Additionally, molybdenum (Mo) in a range from about 0.8 wt % to about 1.0 wt %, vanadium (V) in a range from about 0.4 wt % to about 0.6 wt %, chrome (Cr) in a range from about 0.2 wt % to about 0.4 wt % and niobium (Nb) in a range from about 0.2 wt % to about 0.4 wt % may be added to the molten cast iron. Before tapping the molten cast iron, content of each elements were adjusted using a spectrometer based on compositions listed in Table 1 below.

Then, during the tapping process, Mg treatment was performed, and a Fe—Si based inoculant was injected concurrently with the tapping. After the tapping was finished into a ladle, a temperature of a molten metal was measured, and the molten metal was injected into a mold. A second inoculation was performed concurrently with the injection into the mold, to manufacture heat resistant spheroidal graphite cast iron.

On the other hand, conventional heat resistant spheroidal graphite cast iron was prepared based on compositions listed in Table 1 below. The conventional heat resistant spheroidal graphite cast iron was manufactured by processes similar to those of manufacturing heat resistant spheroidal graphite cast iron in accordance with example embodiments, except for addition of vanadium (V), chrome (Cr) and niobium (Nb).

TABLE 1

| | weight percent (wt %) | | | | | | | |
|---|---|---|---|---|---|---|---|---|
| | C | Si | Mn | Mg | Mo | V | Cr | Nb |
| conventional heat resistant spheroidal graphite cast iron | 2.8-3.7 | 4.0-4.5 | <0.35 | >0.025 | 0.8-1.2 | — | — | — |
| heat resistant spheroidal graphite cast iron according to example embodiments | 3.2-3.4 | 4.3-4.8 | 0.2-0.3 | 0.035-0.05 | 0.8-1.0 | 0.4-0.6 | 0.2-0.4 | 0.2-0.4 |

Then, room temperature tensile strength and high temperature tensile strength (700° C., 800° C.) of heat resistant spheroidal graphite cast iron in accordance with example embodiments and conventional heat resistant spheroidal graphite cast iron were measured. As listed in Table 2, heat resistant spheroidal graphite cast iron in accordance with example embodiments has improved room temperature and high temperature tensile strength due to advanced alloy design technology when compared with the conventional heat resistant spheroidal graphite cast iron.

TABLE 2

| | mechanical properties | | |
|---|---|---|---|
| | room temperature | high temperature tensile strength (MPa) | |
| material | tensile strength (MPa) | 700° C. | 800° C. |
| conventional heat resistant spheroidal graphite cast iron | 632 | 82-92 | 43-55 |
| heat resistant spheroidal graphite cast iron according to example embodiments | 671 | 107 | 66 |

Coefficient of thermal expansion and eutectoid transformation temperature of heat resistant spheroidal graphite cast iron for an engine exhaust system component in accordance with example embodiments were measured using dilatometer and Table 3 below shows measured results. When an engine exhaust system component is heated to reach the eutectoid temperature, eutectoid transformation may occur to cause damage to the product due to lattice change. Therefore, a material technology capable of increasing the eutectoid temperature may be required to be developed. Silicon (Si) may be a main alloy element for increasing the eutectoid temperature, and carbide element such as chrome (Cr) and molybdenum (Mo) may assist in increasing the eutectoid temperature. Accordingly, heat resistant spheroidal graphite cast iron in accordance with example embodiments has improved eutectoid transformation temperature and low coefficient of thermal expansion when compared with the conventional heat resistant spheroidal graphite cast iron.

TABLE 3

| | mechanical properties | |
|---|---|---|
| material | coefficient of thermal expansion (μm/m · ° C.) | eutectoid transformation temperature (E.T.T) |
| conventional heat resistant spheroidal graphite cast iron | 14.7 | 878° C. |

TABLE 3-continued

| | mechanical properties | |
|---|---|---|
| material | coefficient of thermal expansion (μm/m · ° C.) | eutectoid transformation temperature (E.T.T) |
| heat resistant spheroidal graphite cast iron according to example embodiments | 13.2 | 935° C. |

Table 4 represents compositions and high temperature tensile strength (H.T.T.S) of heat resistant spheroidal graphite cast irons of Examples 1 to 7 (Ex. 1 to 7), and Comparative Examples 1 to 6 (C.E. 1 to 6). That is, heat resistant spheroidal graphite cast iron according to example embodiments and comparative examples include carbon (C), silicon (Si), manganese (Mn), phosphorous (P), sulfur (S), magnesium (Mg), molybdenum (Mo), chrome (Cr), niobium (Nb) and barium (Ba). In here, the content ratio of chrome (Cr) and barium (Ba) (Cr/Ba) was varied. In Examples 1 to 7, the amount of chrome (Cr) was in range from about 0.2 wt % to about 0.4 wt %, and the content ratio of chrome (Cr) and barium (Ba) (Cr/Ba) was in a range from about 26 to about 89.

On the other hand, when the amount of barium (Ba) was less than 0.0045 wt % or more than 0.0075 wt % in Comparative Examples 1 to 3, high temperature tensile strength was relatively low.

In Comparative Examples 4 and 5, high temperature tensile strength was relatively low when compared with the present inventive concepts.

In Comparative Example 6, the amount of vanadium (V) was less than 0.4 wt %, and other elements were similar to Examples 1 to 5.

In Comparative Examples 7 and 8, the amounts of chrome (Cr) were 0.13 wt % and 0.72 wt %, respectively. In this case, high temperature tensile strength was relatively low when compared with the present inventive concepts.

In Comparative Examples 9 to 11, the amounts of niobium (Nb) were 0.12 wt %, 0.52 wt % and 0.78 wt % respectively. In this case, high temperature tensile strength was relatively low when compared with the present inventive concepts.

TABLE 4

| | C | Si | Mn | P | S | Mg | Mo | V | Cr | Nb | Ba | Cr/Ba | H.T. T.S/ MPa | E.T. T (° C.) |
|---|---|---|---|---|---|---|---|---|---|---|---|---|---|---|
| Ex. 1 | 3.23 | 4.68 | 0.21 | 0.021 | 0.007 | 0.045 | 0.93 | 0.53 | 0.2 | 0.24 | 0.0075 | 27 | 62 | 921 |
| Ex. 2 | 3.25 | 4.71 | 0.22 | 0.025 | 0.006 | 0.043 | 0.87 | 0.52 | 0.24 | 0.35 | 0.0051 | 47 | 60 | 924 |
| Ex. 3 | 3.24 | 4.80 | 0.22 | 0.024 | 0.007 | 0.037 | 0.94 | 0.55 | 0.32 | 0.35 | 0.0061 | 52 | 62 | 935 |
| Ex. 4 | 3.20 | 4.67 | 0.24 | 0.026 | 0.008 | 0.039 | 1.0 | 0.57 | 0.36 | 0.4 | 0.0054 | 67 | 67 | 920 |
| Ex. 5 | 3.25 | 4.72 | 0.27 | 0.024 | 0.007 | 0.04 | 0.85 | 0.56 | 0.4 | 0.29 | 0.0045 | 89 | 63 | 930 |
| C.E. 1 | 3.24 | 4.4 | 0.24 | 0.026 | 0.007 | 0.046 | 0.95 | 0.51 | 0.26 | 0.33 | 0.015 | 17 | 53 | 910 |
| C.E. 2 | 3.28 | 4.65 | 0.22 | 0.022 | 0.006 | 0.041 | 0.96 | 0.56 | 0.31 | 0.32 | 0.0032 | 97 | 52 | 918 |
| C.E. 3 | 3.25 | 4.52 | 0.21 | 0.025 | 0.007 | 0.043 | 0.99 | 0.52 | 0.32 | 0.28 | 0.0027 | 118 | 49 | 912 |
| C.E. 4 | 3.27 | 4.02 | 0.23 | 0.024 | 0.007 | 0.04 | 0.95 | 0.51 | 0.28 | 0.32 | 0.0062 | 45 | 47 | 873 |
| C.E. 5 | 3.37 | 4.57 | 0.25 | 0.024 | 0.006 | 0.047 | 0.71 | 0.54 | 0.24 | 0.26 | 0.0058 | 41 | 43 | 904 |
| C.E. 6 | 3.27 | 4.41 | 0.25 | 0.027 | 0.005 | 0.045 | 0.87 | 0.38 | 0.22 | 0.34 | 0.0068 | 32 | 45 | 897 |
| C.E. 7 | 3.29 | 4.43 | 0.22 | 0.025 | 0.008 | 0.042 | 0.96 | 0.57 | 0.13 | 0.35 | 0.0047 | 28 | 42 | 903 |
| C.E. 8 | 3.27 | 4.52 | 0.26 | 0.022 | 0.007 | 0.048 | 0.97 | 0.52 | 0.72 | 0.3 | 0.0054 | 133 | 43 | 909 |
| C.E. 9 | 3.3 | 4.58 | 0.21 | 0.024 | 0.006 | 0.036 | 0.89 | 0.55 | 0.35 | 0.12 | 0.0068 | 51 | 44 | 910 |
| C.E. 10 | 3.25 | 4.38 | 0.24 | 0.027 | 0.008 | 0.042 | 0.90 | 0.58 | 0.28 | 0.52 | 0.0049 | 57 | 42 | 893 |
| C.E. 11 | 3.22 | 4.72 | 0.23 | 0.026 | 0.009 | 0.046 | 0.97 | 0.54 | 0.27 | 0.78 | 0.007 | 39 | 46 | 925 |

Figure 3:
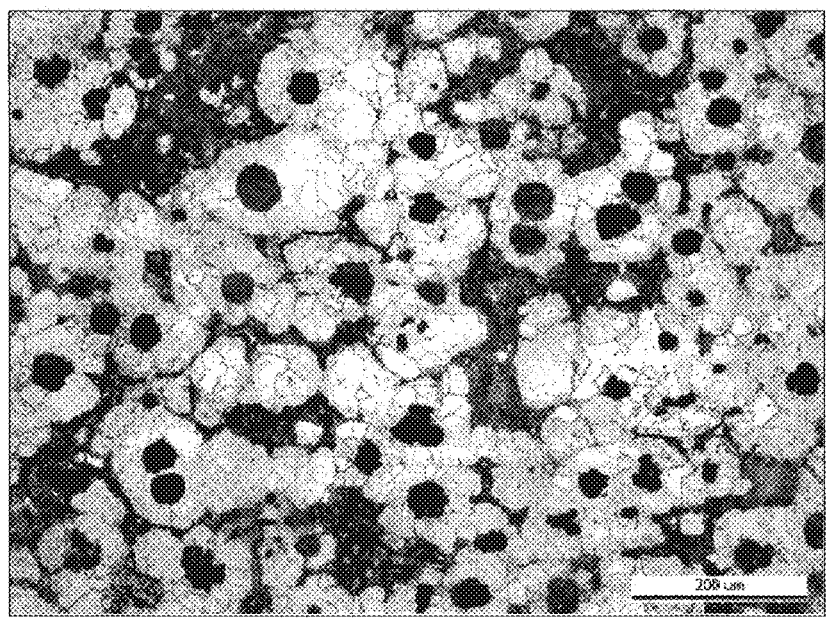
FIGS. 3 and 4 are optical microscope images illustrating microstructures of heat resistant spheroidal graphite cast iron in accordance with example embodiments.
Figure 4:
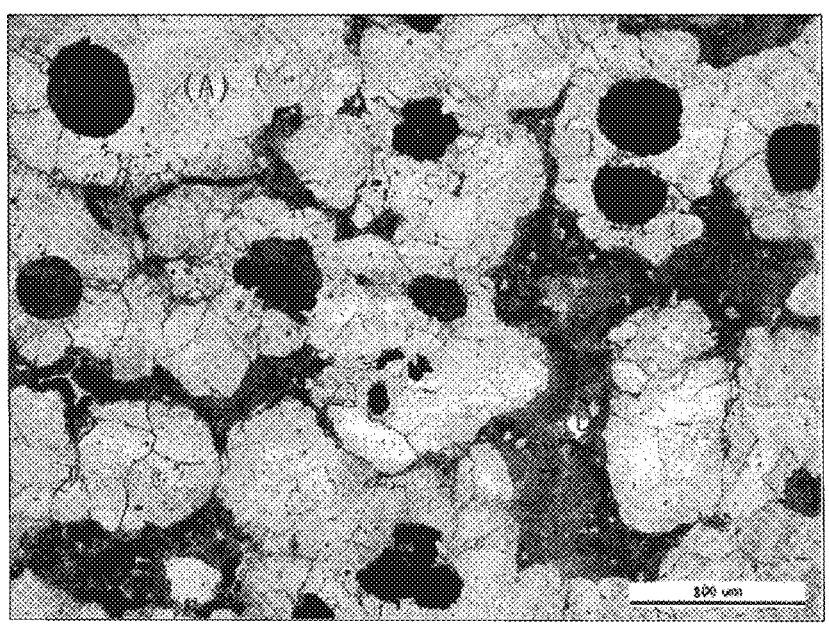

FIGS. 3 and 4 are images illustrating microstructures of heat resistant spheroidal graphite cast iron in accordance with example embodiments.

Referring to FIGS. 3 and 4, the heat resistant spheroidal graphite cast iron may include a ferrite structure (A) which occupies an area of about 50% or more in the images as shown in white and a pearlite structure (B) which occupies an area of about 40% or less in the images as shown in black. In FIGS. 3 and 4, graphite (C), which is precipitated in the ferrite structure and has a spheroidal shape, was observed and carbide (D), which is precipitated in the pearlite structure and is shown in a bright color, was observed. The carbide was chrome carbide, vanadium carbide and niobium carbide, and the carbide may improve high temperature material properties of the heat resistant spheroidal graphite cast iron.

Figure 5:
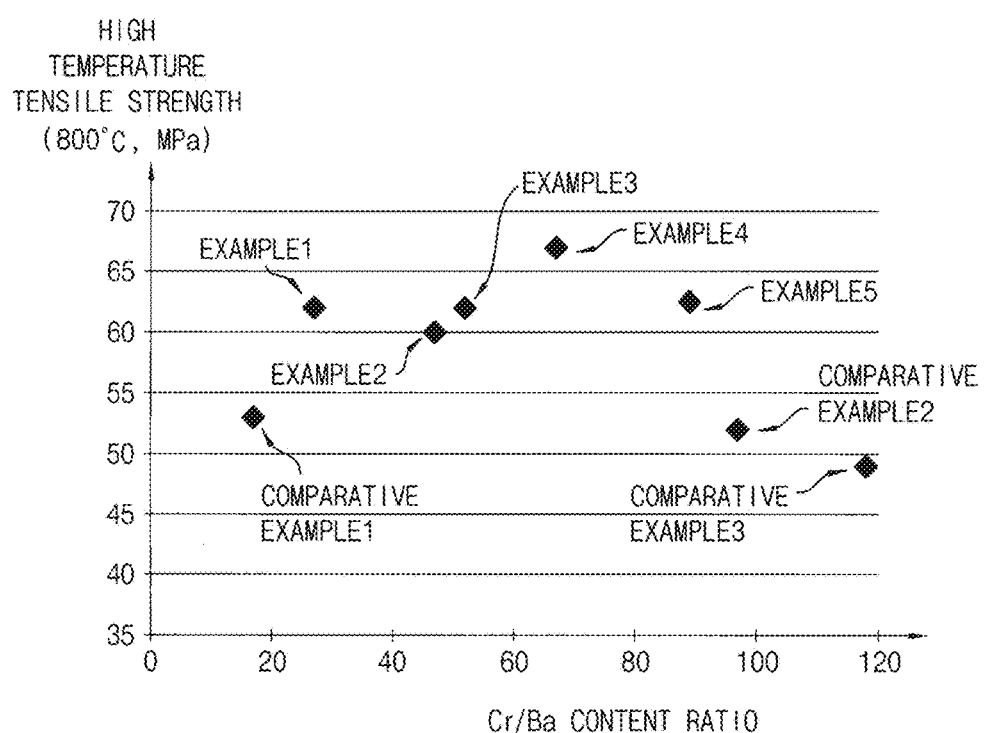
FIG. 5 is a graph illustrating high temperature tensile strength at a temperature of 800° C. of heat resistant spheroidal graphite cast iron of Examples and Comparative Examples.

FIG. 5 is a graph illustrating high temperature tensile strength at a temperature of 800° C. of heat resistant spheroidal graphite cast iron of Examples and Comparative Examples. Referring to FIG. 5 and Table. 4, when the amount of chrome (Cr) is in a range from about 0.2 wt % to about 0.4 wt % and the content ratio of chrome (Cr) and barium (Br) (Cr/Ba) is in a range from about 26 to about 89, high temperature tensile strength of the heat resistant spheroidal graphite cast iron may have a relatively high value of about 59 MPa or more at a temperature of about 800° C. On the other hand, the heat resistant spheroidal graphite cast iron of Comparative Examples 1 to 3 has high temperature tensile strength of about 49 Mpa or less at a temperature of about 800° C. Especially, when the content ratio of chrome (Cr) and barium (Br) (Cr/B a) exceeds about 89, chrome carbide may be increased over a proper content ratio, so that brittleness and machinability at a room temperature may be decreased and inoculation ability may be decreased. Consequently, the content ratio of chrome (Cr) and barium (Ba) of the second composition of the heat resistant spheroidal graphite cast iron may be controlled to thereby improve high temperature tensile strength by 20% or more.

Figure 6:
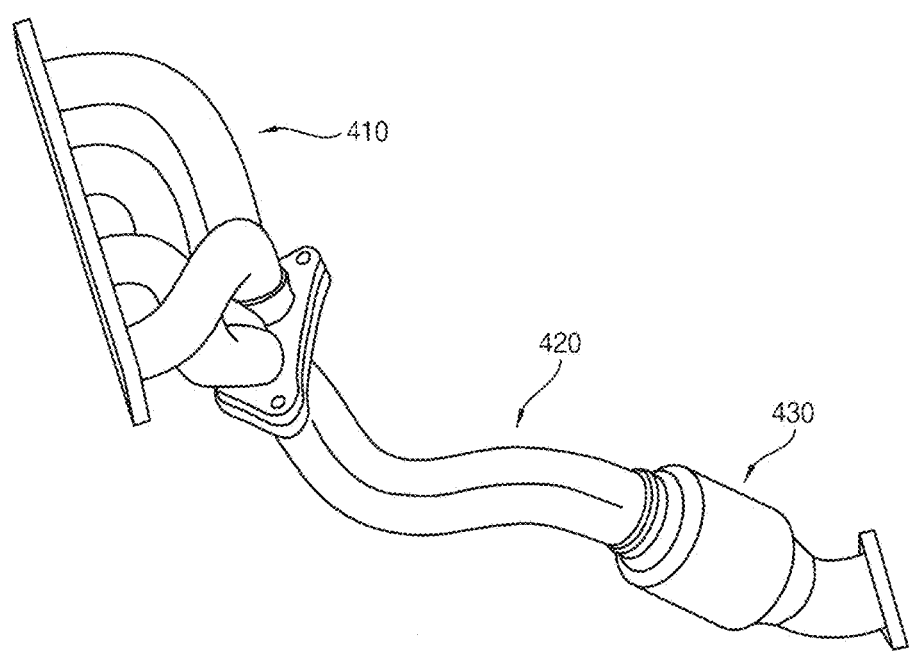
FIG. 6 illustrates an engine exhaust system including a heat resistant spheroidal graphite cast iron in accordance with example embodiments.

FIG. 6 illustrates an engine exhaust system including heat resistant spheroidal graphite cast iron in accordance with example embodiments.

An engine exhaust system component may include an exhaust manifold 410 connected to an exhaust port (not illustrated) of a combustion chamber per each cylinder, a front pipe 420 coupled to a rear end of the exhaust manifold 410, and a vibration compensation device 430 installed in an outer periphery of the front pipe 420 and absorbing a vibration due to a shock wave during an exhaustion.

Particularly, the exhaust manifold 410 may contact a high temperature exhaust gas discharged from the combustion chamber, and thus may be required to have an excellent heat-resistance. According to example embodiments, the exhaust manifold 410 may include the heat resistant spheroidal graphite cast iron of the present inventive concepts.

INDUSTRIAL APPLICATION

Heat resistant spheroidal graphite cast iron in accordance with example embodiments of the present inventive concepts may include vanadium (V), chrome (Cr) and niobium (Nb) as well as barium (Ba). In addition, the content ratio of chrome (Cr) and barium (Ba) may controlled such that chrome carbide showing embrittlement at a room temperature may be prevented from being generated and graphite nucleation creation may be facilitated, to thereby provide the heat resistant spheroidal graphite cast iron having a stable material property and structure. Because the heat resistant spheroidal cast iron has an improved high temperature tensile strength, the heat resistant spheroidal graphite cast iron may be effectively implemented to the exhaust manifold in an engine exhaust system which operates under high temperature.

The foregoing is illustrative of example embodiments and is not to be construed as limiting thereof. Although a few example embodiments have been described, those skilled in the art will readily appreciate that many modifications are possible in example embodiments without materially departing from the novel teachings and advantages of the present invention. Accordingly, all such modifications are intended to be included within the scope of example embodiments as defined in the claims.

* Description of Reference numerals

| | |
|---|---|
| 100: melting furnace | 110: first molten cast iron |
| 120: second molten cast iron | 200: ladle |
| 210: first inoculant | 220: second incoulant |
| 300: mold | 310: injection portion |
| 315: pouring basin | 320: mold body |
| 330: injection passage | 410: exhaust manifold |
| 420: front pipe | 430: vibration compensation device |

What is claimed is:

1. A heat resistant spheroidal graphite cast iron for an engine component, comprising:
   carbon (C) in a range from 3.2 weight percent to 3.4 weight percent, silicon (Si) in a range from 4.3 weight percent to 4.8 weight percent, manganese (Mn) in a range from 0.2 weight percent to 0.3 weight percent, molybdenum (Mo) in a range from 0.8 weight percent to 1.0 weight percent, vanadium (V) in a range from 0.4 weight percent to 0.6 weight percent, chrome (Cr) in a range from 0.2 weight percent to 0.4 weight percent, niobium (Nb) in a range from 0.2 weight percent to 0.4 weight percent, barium (Ba) in a range from 0.0045 weight percent to 0.0075 weight percent, inevitable impurities, and a remainder of iron (Fe), based on a total weight of the heat resistant spheroidal graphite cast iron,
   wherein a content ratio of chrome (Cr) and barium (Ba) (Cr/Ba) is in a range from 26 to 89.

2. The heat resistant spheroidal graphite cast iron of claim 1, wherein the heat resistant spheroidal graphite cast iron has tensile strength of about 670 Mpa or more at a room temperature, and has high temperature tensile strength of 100 Mpa or more at 700° C. and of 59 Mpa or more at 800° C.

3. The heat resistant spheroidal graphite cast iron of claim 1, wherein the heat resistant spheroidal graphite cast iron has a thermal expansion coefficient of about 13.5 μm/m·° C. or less, and has eutectoid transformation temperature of from about 920° C. to about 940° C.

4. The heat resistant spheroidal graphite cast iron of claim 1, wherein the heat resistant spheroidal graphite cast iron has high temperature tensile strength of from 59 Mpa to 70 Mpa at 800° C.

5. The heat resistant spheroidal graphite cast iron of claim 1, wherein the heat resistant spheroidal graphite cast iron comprises a ferrite structure occupying an area of about 50% or more and a pearlite structure occupying an area of 40% or less in a total area, and
   wherein graphite having a spheroidal shape is precipitated in the ferrite structure and carbide is precipitated in the pearlite structure.

6. A component of engine exhaust system comprising the heat resistant spheroidal graphite cast iron according to claim 1.

7. A method of manufacturing heat resistant spheroidal graphite cast iron, comprising:
   forming a molten cast iron including carbon (C) in a range from about 3.2 weight percent to about 3.4 weight percent, silicon (Si) in a range from about 4.3 weight percent to about 4.8 weight percent, manganese (Mn) in a range from about 0.2 weight percent to about 0.3 weight percent, molybdenum (Mo) in a range from about 0.8 weight percent to about 1.0 weight percent, vanadium (V) in a range from about 0.4 weight percent to about 0.6 weight percent, chrome (Cr) in a range from about 0.2 weight percent to about 0.4 weight percent, niobium (Nb) in a range from about 0.2 weight percent to about 0.4 weight percent, inevitable impurities, and a remainder of iron (Fe), based on a total weight;
   tapping the molten cast iron into a ladle; and
   injecting the tapped molten cast iron into a mold
   wherein, prior to injecting the tapped molten cast iron into the mold, barium (Ba) is added into the molten cast iron in a range from about 0.0045 weight percent to about 0.0075 weight percent, and a content ratio of chrome (Cr) and barium (Ba) (Cr/Ba) is in a range from about 26 to 89.

8. The method of claim 7, wherein tapping the molten cast iron into the ladle comprises adding a first inoculants into the molten cast iron, and wherein injecting the tapped molten cast iron into the mold comprises adding a second inoculant into the molten cast iron.

9. The method of claim 7, wherein forming the molten cast iron comprises forming a preliminary molten cast iron;
analyzing the preliminary molten cast iron by a thermal analysis or a mass spectrometer; and
adding a deficient ingredient into the preliminary molten cast iron.

* * * * *